US00PP36896P2

(12) United States Plant Patent
Lim

(10) Patent No.: US PP36,896 P2
(45) Date of Patent: Aug. 19, 2025

(54) ***HIBISCUS* PLANT NAMED 'ALTodired'**

(50) Latin Name: *Hibiscus rosa-sinensis*
Varietal Denomination: ALTodired

(71) Applicant: Altman Specialty Plants llc, Vista, CA (US)

(72) Inventor: Peter Lim, Escondido, CA (US)

(73) Assignee: Altman Specialty Plants llc, Vista, CA (US)

( * ) Notice: Subject to any disclaimer, the term of this patent is extended or adjusted under 35 U.S.C. 154(b) by 0 days.

(21) Appl. No.: 19/022,344

(22) Filed: Jan. 15, 2025

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./226, 257
See application file for complete search history.

(56) References Cited

U.S. PATENT DOCUMENTS

PP34,782 P2 * 11/2022 Berry ..... Plt./257

* cited by examiner

*Primary Examiner* — Karen M Redden
(74) *Attorney, Agent, or Firm* — Cassandra Bright

(57) ABSTRACT

A new and distinct cultivar of *Hibiscus* plant named 'ALTodired' is disclosed, characterized by hot pink flowers with a small red center and a thin creamy yellow picotee. Plants are bushy and compact reaching about 3 feet tall. Flowers diameter is around 15 cm. The new variety is a *Hibiscus*, typically produced as an ornamental plant.

1 Drawing Sheet

Latin name of the genus and species: *Hibiscus rosa-sinensis.*

Variety denomination: 'ALTodired'.

BACKGROUND OF THE INVENTION

The new *Hibiscus* cultivar is a product of a planned breeding program conducted by the inventor, Peter Lim. The objective of the breeding program was to produce vigorous *Hibiscus rosa-sinensis* cultivars with healthy foliage. The cross resulting in this new variety was made Aug. 28, 2016.

The seed parent is *Hibiscus rosa-sinensis* 'Leading Lady' ('JGB 14007'; U.S. Plant Pat. No. 31,302). The pollen parent is the unpatented variety of *Hibiscus rosa-sinensis* 'Social Butterfly'. The new variety was identified and selected as a potentially interesting selection in July of 2019. Selection was made at a commercial nursery in Vista, California.

Asexual reproduction of the new cultivar 'ALTodired' was first performed Sep. 13, 2020 in Vista, California, by vegetative cuttings. Subsequent propagation has shown that the unique features of this cultivar are stable and reproduced true to type in successive generations.

SUMMARY OF THE INVENTION

The cultivar 'ALTodired' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTodired'. These characteristics in combination distinguish 'ALTodired' as a new and distinct *Hibiscus* cultivar:

1. Hot pink flowers with a small dark red center and a thin creamy yellow picotee.
2. Flower diameter around 15 cm.
3. Compact, bushy plants of about 3 feet tall.
4. Large, cordate foliage.

PARENT COMPARISONS

Plants of the new cultivar 'ALTodired' are similar to the seed parent, in most horticultural characteristics. However, characteristics of the new cultivar differ in the following:

1. The new cultivar is about 1 foot shorter than plants of the seed parent.
2. Flowers of the new cultivar are hot pink flowers of 'Leading Lady' are yellow with a white center.

Plants of the new cultivar 'ALTodired' are similar to the pollen parent, in most horticultural characteristics. However, characteristics of the new cultivar differ in the following:

1. The new cultivar is about 1 to 2 feet shorter than plants of the pollen parent.
2. Flowers of the new cultivar are hot pink flowers of 'Social Butterfly' are golden yellow with a red center and white veins.

COMMERCIAL COMPARISON

Plants of 'ALTodired' are similar in some horticultural characteristics to the variety *Hibiscus* 'JBG 13008', U.S. Plant Pat. No. 34,782 The new variety, however, differs in the following:

1. Flowers of 'ALTodired' are hot pink with a small red center; flowers of this comparator are red.
2. Flower petals of the new cultivar do not reflex back as strongly as petals of this comparator.

3. Flower petals of the new cultivar strongly overlap, petal of this comparator weakly overlap.

Plants of 'ALTodired' are similar in some horticultural characteristics to the variety *Hibiscus* 'America's Sweetheart', unpatented. The new variety, however, differs in the following:

1. Flowers of 'ALTodired' are hot pink with a small red center, flowers of this comparator are medium lavender pink with significant white streaking.
2. Stigma color of 'ALTodired' is bright red; stigma color of this comparator is golden yellow.
3. Foliage of the new cultivar is darker than foliage of this comparator.

BRIEF DESCRIPTION OF THE PHOTOGRAPH

The accompanying photograph illustrates in full color a typical flower of 'ALTodired' from a plant grown outdoors at a commercial nursery in Vista, California. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe a 'ALTodired' plant. This plant was grown at a commercial nursery in Vista, California. The growing temperature ranged from about 7° C. to 30° C. during the day and from about 5° C. to 12° C. during the night. No artificial light, photoperiodic treatments were given to the plants. Measurements and numerical values represent averages of typical plant types.

Botanical classification: *Hibiscus rosa-sinensis* 'ALTodired'.

PROPAGATION

Typical method: Hardwood stem cuttings.

Root description: Roots are fine, fibrous and well branched. Tan/brown in color, not effectively measured with a color chart.

PLANT

Plant type: Tender, woody flowering shrub.

Age of plant described: Approximately 1.5 years old.

Growth habit: Compact.

Height: 70 cm.

Plant spread: 60 cm.

Branching characteristics: 2 to 4 breaks from a pinch, occurring at an average 45° angle.

Length of primary lateral branches: 25 to 65 cm.

Quantity of lateral branches: Each primary lateral branch has 4 to 8 laterals.

Characteristics of primary lateral branches:

*Diameter.*—Average range 12 to 17 mm.

*Color.*—New growth RHS Green N137D. Mature growth RHS Greyed-Green 197B, striated Grey-Brown N199A.

*Texture.*—New growth very sparsely hirsute, older growth striated.

Internode length: Average range 2.5 to 3.2 cm.

FOLIAGE

Leaf:

*Arrangement.*—Alternate.

*Quantity.*—Average 12 to 20 per branch.

*Leaf internode.*—1 cm.

*Average length.*—10 to 14 cm, excluding petiole.

*Average width.*—10 to 12 cm.

*Shape of blade.*—Cordate.

*Apex.*—Acute.

*Base.*—Obtuse.

*Margin.*—Entire or irregularly and shallowly crenate.

*Aspect.*—Strongly undulating.

*Texture of top surface.*—Glabrous.

*Texture of bottom surface.*—Sparse and very short hirsute.

*Color.*—Young foliage upper side: RHS Green 139A. Young foliage under side: RHS Green 137A. Mature foliage upper side: RHS Green 139A overlayed Greyed-Green N189A. Mature foliage under side: RHS Green 137A.

*Venation.*—Type: Pinnate. Venation color, upper side: RHS Green 138B. Venation color, under side: RHS Green 138B.

*Petiole.*—Length: 2.5 to 3.2 cm. Diameter: 5 mm. Color: Near RHS Green 138A. Texture: Densely short hirsute.

*Leaf stipule.*—Not observed.

FLOWER

Natural flowering season: Nearly year round in Southern California.

Flower type and habit: Solitary, rotate.

*Single, double, multiplex.*—Single.

*Petals overlapping.*—Strongly overlapping.

Quantity of flowers: A plant of about 2 years old has approximately 30 open flowers at one time during Summer.

Rate of flower opening: 4 to 6 days from bud to fully opened flower.

Flower longevity on plant: 3 days.

Persistent or self-cleaning: Self-cleaning.

Bud:

*Shape.*—Ovate.

*Length.*—6 cm.

*Diameter.*—2.8 cm.

*Color.*—RHS Green N137D.

Flower size:

*Diameter.*—15 cm.

*Depth.*—8 cm.

Petals:

*Quantity.*—5.

*Arrangement.*—Whorled, strongly overlapping.

*Length.*—10 cm.

*Width.*—8 cm.

*Shape.*—Slightly asymmetrical broad spatulate.

*Apex.*—Obtuse rounded with irregular, shallow crenations.

*Base.*—Attenuate.

*Margin.*—Entire. Moderate undulation.

*Texture.*—Glabrous all surfaces. Strongly rugose top and bottom.

*Color*.—When opening, upper surface: RHS Red 47A flushed 53B. Small basal blotch (forming flower eye) Greyed-Purple N186C. Veins Red 51C. Thin picotee colored near Yellow 13D. When opening, lower surface: RHS Red 48C flushed 54D. Veins Red 50D. Very thin picotee colored near Orange 27D. Fully opened, upper surface: RHS Red 53C subtly flushed Red-Purple 58A and 59D. Small basal blotch (forming flower eye) Red-Purple 59A. Veins Red 50D. Thin picotee colored near Yellow 13D. Fully opened, lower surface: RHS Red 49C flushed 56A. Veins Red 50D. Thin picotee colored near yellow 13D. Ratio of basal blotch/eye to petal size: Overall 10% of the upper petal blade is blotched. Feathering: No significant feathering.

Sepals:

*Quantity*.—5.
*Length*.—2.5 cm.
*Width*.—1.5 cm.
*Shape*.—Oblanceolate.
*Margin*.—Entire.
*Apex*.—Acute.
*Base*.—Fused.
*Color*.—Upper surface: RHS Green 138A. Lower surface: RHS Green 138A.
*Texture*.—Upper surface: Softly pubescent. Lower surface: Very short hirsute.

Epicalyx:

*Quantity of bracts*.—6.
*Bract length*.—1.2 cm to 1.5 cm.
*Bract width*.—3 to 4 mm.
*Bract shape*.—Straplike.
*Bract margin*.—Entire.
*Color*.—Upper surface: RHS Green 138A. Lower surface: Near RHS Green 138B.
*Texture*.—Upper surface glabrous, lower surface non-pubescent rough.

Peduncles:

*Length*.—4 cm.
*Diameter*.—6 mm.
*Angle*.—Approximately 45° to the lateral branch.
*Strength*.—Strong.
*Texture*.—Sparsely hirsute.
*Color*.—RHS Green 138A.

Fragrance: Faint musty scent.

REPRODUCTIVE ORGANS

Stamens:

*Number*.—About 60 to 70.
*Filament length*.—11 mm.
*Filament color*.—Near Red 53C.

Anthers:

*Shape*.—Irregular sphere.
*Length*.—About 3 mm.
*Color*.—Near RHS Yellow 13C.
*Pollen color*.—Near RHS Yellow 13C.
*Pollen amount*.—Scant.

Pistil:

*Number*.—1.
*Length*.—8 cm.
*Style*.—Length: 7 cm. Color: Lower section near Greyed-Purple N186D, mid-section Red 53C. Uppermost ⅓ Red-Purple N57B.
*Stigma*.—Shape: Peltate. Color: Near RHS Red 53C.
*Ovary color*.—Near RHS Red 52A.
*Ovary length*.—1.5 cm 9.
*Ovary width*.—8 mm.

OTHER CHARACTERISTICS

Seeds: Not observed.

Disease/pest resistance: Neither resistance nor susceptibility to normal diseases and pests of *Hibiscus rosa-sinensis* have been observed.

Temperature tolerance: USDA Zones 8 through 11.

What is claimed is:

1. A new and distinct cultivar of *Hibiscus* plant named 'ALTodired' as herein illustrated and described.

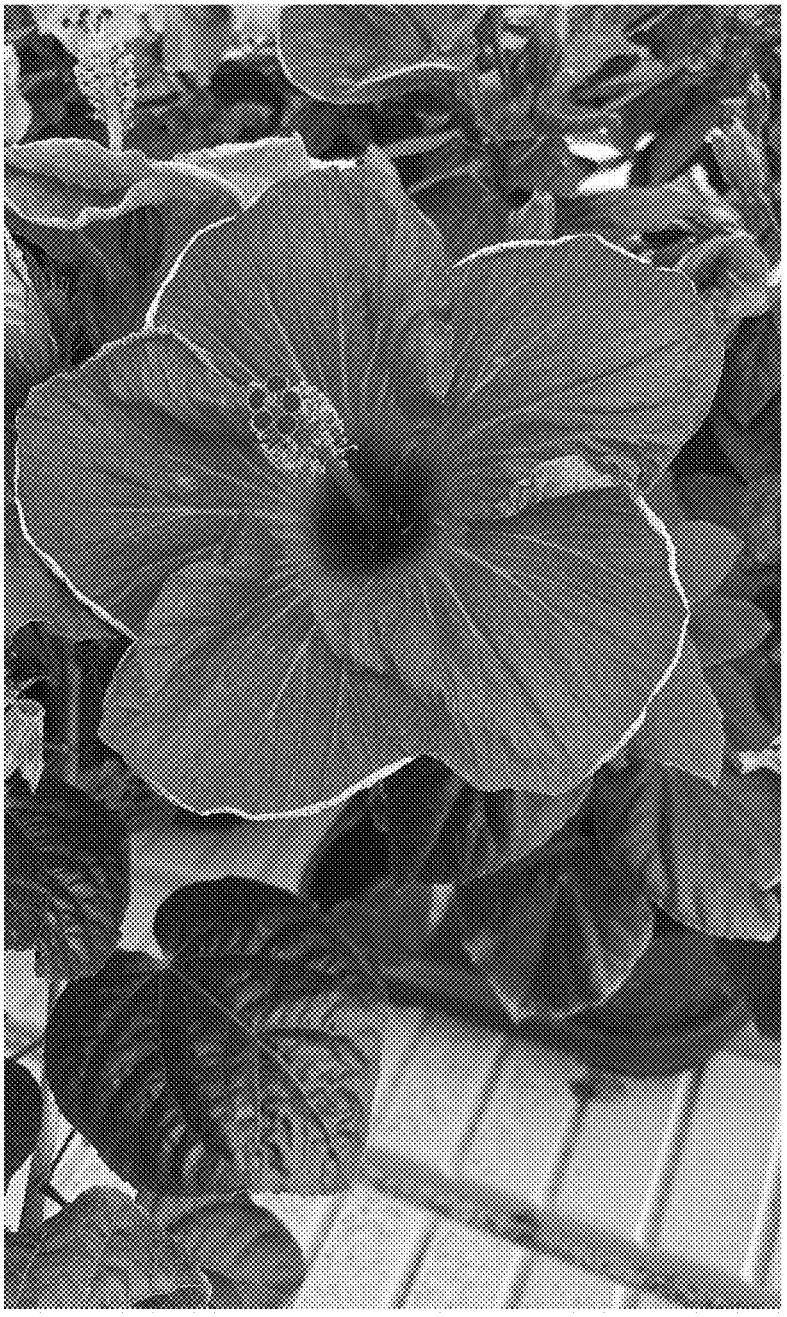

* * * * *